United States Patent [19]

Traas et al.

[11] 4,235,824

[45] Nov. 25, 1980

[54] METHOD FOR THE PREPARATION OF FRAGRANCES, AND METHOD FOR THE PREPARATION OF PERFUME COMPOSITIONS

[75] Inventors: Petrus C. Traas, Naarden; Harmannus Boelens, Huizen; Hans J. Wille, Bussum, all of Netherlands

[73] Assignee: Naarden International N.V., Naarden-Bussum, Netherlands

[21] Appl. No.: 959,233

[22] Filed: Nov. 9, 1978

Related U.S. Application Data

[62] Division of Ser. No. 817,914, Jul. 22, 1977.

[30] Foreign Application Priority Data

Jul. 27, 1976 [NL] Netherlands ......................... 7608333

[51] Int. Cl.$^3$ ............................................ C07C 47/222
[52] U.S. Cl. ..................................... 568/486; 568/597
[58] Field of Search ..................... 260/601 R; 568/597

[56] References Cited

U.S. PATENT DOCUMENTS

| 2,583,194 | 1/1952 | Weisler ............................ 260/563 R |
| 3,157,660 | 11/1964 | Stilz et al. ............................ 546/176 |
| 3,168,550 | 2/1965 | Blumenthal ......................... 260/464 |
| 3,531,510 | 9/1970 | Blumenthal ....................... 260/465.9 |
| 3,655,722 | 4/1972 | Mitchell et al. .................. 260/465.9 |
| 3,700,717 | 10/1972 | Kappeler et al. ................. 260/465.2 |
| 3,824,319 | 7/1974 | Schwartz et al. ..................... 424/278 |

FOREIGN PATENT DOCUMENTS

| 482637 | 1/1970 | Switzerland ......................... 260/601 R |
| 503678 | 4/1971 | Switzerland ......................... 260/601 R |
| 1068712 | 5/1967 | United Kingdom ................ 260/601 R |
| 1211697 | 11/1970 | United Kingdom ................ 260/601 R |
| 1257111 | 12/1971 | United Kingdom ................ 260/601 R |

OTHER PUBLICATIONS

Sondheimer, J. Amer. Chem. Soc., vol. 74, pp. 4040–4042.
Jutz, "Chem. Ber." vol. 92, 1983–1989 (1959).
Kirk-Othmer "Encyclopedia of Chem. Tech." vol. 12 pp. 154 & 262.
"Perfume and Flavor Chemicals" Arctander (1969) 1505, 1506, 2338–2342.
Sondheimer "J. Amer. Chem. Soc." vol. 74, 4040 (1952).
Seifert et al. "J. Agr. Food Chem", vol. 16, p. 880 (1968).

*Primary Examiner*—Werren B. Lone
*Attorney, Agent, or Firm*—Brumbaugh, Graves, Donohue & Raymond

[57] ABSTRACT

The invention relates to a method for the preparation of both known and novel fragrances and flavors, and in particular to the preparation and use of the novel fragrance compound, 2,6-nonadiene nitrile, and to a novel method for the preparation of 4-heptynal as the starting product for the preparation of the 2,6-nonadiene nitrile fragrance compound.

4 Claims, No Drawings

METHOD FOR THE PREPARATION OF FRAGRANCES, AND METHOD FOR THE PREPARATION OF PERFUME COMPOSITIONS

This is a division of application Ser. No. 817,914, filed July 22, 1977.

The invention relates to a new method for the preparation of known fragrances and flavours, to a method for the preparation of a novel fragrance and to a method for the preparation of perfume compositions and perfumed products.

More specifically the invention relates to a new method for the preparation of 4-heptynal, this compound being a valuable starting product for the preparation of the following known fragrances and flavours: cis-4-heptenal, 2,6-nonadienal and 2,6-nonadienol.

The invention further relates to the preparation of 2,6-nonadiene nitrile as a novel fragrance and to the use of this compound in perfume compositions and perfumed articles and materials. 4-Heptenal, 2,6-nonadienal and 2,6-nonadienol are valuable perfumes and flavours (see for example S. Arctander, Perfume and Flavor Chemicals, Montclair (1969), monograph no. 1505, 2339 and 2341). For these compounds, various multi-step syntheses are known, often starting from the costly compound 3-hexenol. Thus, the preparation of cis-4-heptenal is described in the British Pat. No. 1,068,712 and the preparation of 2,6-nonadienol and nonadienal by Ch. Jutz in Chem. Ber. 92, 1983 (1959). Both of the last mentioned compounds can also be prepared from hexadiyne-1,5 as a starting product (F. Sondheimer, J. Am. Chem. Soc. 74, 4040 (1952) and the U.S. Pat. No. 2,855,441) or from cis-4-heptenal (R. M. Seifert and R. G. Buttery, J. Agr. Food Chem. 16, 880 (1968)).

Essentially, 4-heptynal is an attractive starting product for the preparation of the aforesaid fragrances and flavours. So far, however, this compound could be prepared only by starting from 2-ethyl-2-cyclopentenone which is difficult to obtain. Methods for preparing 4-heptynal are described in the Swiss Pat. Nos. 503,678 and 482,637. Moreover, the latter mentions the reduction of 4-heptynal to cis-4-heptenal.

It has now been found that 4-heptynal (formula 1, see reaction scheme A on the formula sheet) can easily be prepared from the easily accessible compounds butyn-1 and acrolein.

Cis-4-heptenal can be prepared from 4-heptynal by catalytic hydrogenation with the aid of a Lindlar catalyst. 2,6-nonadienal can be prepared from cis-4-heptenal, e.g. according to the Seifert and Buttery method (see above) or by means of a Wittig-reaction with formyl methylene triphenyl phosphorane. Similarly nonene-2-yn-6-al can be prepared from 4-heptynal and then converted into 2,6-nonadienal by means of catalytic reduction.

Besides, it has been found that 4-heptynal is a most suitable starting product for the preparation of the novel valuable fragrance 2,6-nonadiene nitrile.

For that purpose, 4-heptynal can first be reduced to cis-4-heptenal and this compound can then converted into 2,6-nonadiene nitrile. Also, 4-heptynal may be converted into nonene-2-yn-6al and subsequently into 2,6-nonadiene nitrile.

It has been found that the novel compound 2,6-nonadiene nitrile is a powerful perfume with an intensive green odour reminiscent of cucumber and with clearly recognizable mignonette-like notes. It is known that the odour of nitriles often resembles that of the corresponding aldehydes but with the advantage of a far superior chemical stability, particularly in alkaline mediums such as soap. Often, however, they have the disadvantage that their olfactory qualities (for use as a perfume) are definitely inferior to those of the corresponding aldehydes due to lack of the natural odour character and to the presence of undesirable odour notes, defined by the perfumer as "chemical" or "chemical-like" (cf. e.g. S. Arctander, monograph no. 649 with no. 1451 and no. 1435 with no. 1439).

Surprisingly, these undesirable odour aspects appear to be entirely absent with 2,6-nonadiene nitrile while the odour character is even far more natural than that of the corresponding aldehyde in the 6-cis-2-trans form (the configuration of highest olfactory value, see S. Arctander, monograph no. 2339). Moreover, 2,6-nonadiene nitrile has a far more persisting odour than the corresponding aldehyde.

According to the invention, 4-heptynal is prepared from butyn-1 and acrolein as indicated in the reaction scheme A on the formula sheet, wherein HX is a hydrogen halide, preferably HBr, and ROH represents a lower aliphatic or araliphatic alcohol having at most 8 carbon atoms, such as methanol, ethanol, propanol, isopropanol, butanols, benzyl alcohol, etc. Both alcohol molecules required in the first reaction step of the reaction scheme A may together represent one aliphatic diol, due to which the acetal obtained (formula 2, reaction scheme A) will then be a cyclic acetal. Examples of such diols are: ethylene glycol and 1,2- of 1,3-propylene glycol. "Me" in the reaction scheme A, stands for an alkali metal, preferably Na or Li, the latter being the more appropriate.

Preparation of the $\alpha$-halopropionaldehyde dialkylacetal (formula 2) may be effected in an appropriate organic solvent, or also without the addition of a solvent. An excess of the alcohol ROH to be used (or the diol 2.ROH) may serve most suitably as a solvent. The reaction may be carried out at temperatures between $-80°$ and $+80°$ C. and preferably between $-20°$ and $+30°$ C.

Preparation of the alkali metal butynilide (formula 3) from butyn and alkali metal amide may be effected in polar solvents such as liquid ammonia, dimethyl formamide, dimethyl sulfoxide, tetrahydrofurane, dioxane, dimethoxyethane, hexa-methylphosphortriamide. Preferably liquid ammonia is used, with the possibility of preparing the alkali metal amide in advance by adding the required quantity of alkali metal to the liquid ammonia.

By adding $\alpha$-halopropionaldehyde dialkylacetal to the alkali metal butynilide solution obtained in the previous reaction step, the 4-heptynal dialkylacetal (formula 4) is formed. Both these reaction steps can be carried out at temperatures between $-80°$ and $+80°$ C. When liquid ammonia is used as a solvent at temperatures over $-33°$ C., the reactions should be carried out at elevated pressure.

Finally, to obtain 4-heptynal, the dialkylacetal can be hydrolyzed in a way commonly used for similar compounds, e.g. with oxalic acid in a water-acetone mixture.

If desired, the 4-heptynal thus obtained can be converted into cis-4-heptenal by catalytic reduction with the aid of a Lindlar catalyst. If desired, 4-heptynaldialkylacetal may first be hydrogenated in the same way and then hydrolyzed to 4-heptenal.

Preparation of 2,6-nonadiene nitrile from 4-heptynal can be effected according to reaction schemes B or C.

According to reaction scheme B, 4-heptynal is reacted with cyanoacetic acid to 2-cyano-3-hydroxy-6-nonynic acid (formula 5). From this, as a result of dehydration and decarboxylation, nonene-2-yn-6-nitrile (formula 6) is obtained which is then converted into 2,6-nonadiene nitrile (formula 7) by catalytic reduction with the aid of a Lindlar catalyst.

According to reaction scheme C, 4-heptynal is reacted with cyanomethyl diethyl phosphonate (formula 8), which may be prepared from triethyl phosphite and chloroacetonitrile. If desired, another cyanomethyl dialkyl phosphonate may be used instead of cyanomethyl diethyl phosphonate.

The reactions of reaction schemes B and C can also be applied to cis-4-heptenal, in which case 2,6-nonadiene nitrile will be formed directly instead of nonene-2-yn-6-nitrile.

It will be understood by one skilled in the art that 2,6-nonadiene nitrile may be prepared by various other methods usual for similar compounds, e.g. from the corresponding aldehyde via the oxime and dehydration of the latter.

As is known for the corresponding aldehyde, the 6-cis-nitrile has the best olfactory properties. Preferably, therefore, the nonadiene nitrile to be used will essentially possess the 6-cis structure. The synthesis via catalytic reduction of an acetylene compound with the aid of a Lindlar catalyst yields a sufficiently high 6-cis-nitrile percentage, so that elimination of the 6-trans material, that is still present, even though possible, will not be necessary in practice.

The nonadiene nitrile according to the invention can be used as such as a perfume or may be combined with other single fragrances and/or mixtures (such as essential oils) to provide a perfume composition. By the phrase "perfume composition" a mixture of perfumes and auxiliary substances is meant, said mixture being dissolved, if desired, in an appropriate solvent or mixed with a powdered substrate which is used to impart the desired odour to a wide variety of materials and articles. Such articles are e.g.: soaps, detergents, cleaners, cosmetics, room deodorants etc.

The amount of nonadiene nitrile according to the invention that may be used varies within ample limits and is dependent on the odour effect to be achieved and, in case of perfume compositions, on the nature and the amount of the other components. The amount of nitrile applied will preferably vary between 0.001% and 40% by weight for concentrated perfume compositions but may, of course, be proportionally less in dilutions or when used in a product to be perfumed, where amounts of 0.0001% and lower may be sufficient.

The following examples illustrate the preparation and application of the compounds according to the invention.

EXAMPLE I

Preparation of 4-heptynal

A—α-bromopropionaldehyde dimethylacetal 240 g (7.5 mol) of methanol in a 1 l reaction vessel was cooled to 5° C., after which 202 g (2.5 mol) of HBr was introduced in 1.5 hrs. At the same temperature 140 g (2.5 mol) of acrolein was then added in 1.5 hrs and the mixture was stirred during another 1.5 hrs. The reaction mixture divided into two layers. The lower layer, consisting of raw α-bromopropionaldehyde dimethylacetal, was separated. The methanolic upperlayer was diluted with 300 ml of water, after which the mixture again divided into two layers. The lower layer was again separated and combined with the α-bromopropionaldehyde dimethylacetal already obtained. The acetal thus obtained (285 g) was stirred with 10 g of soda and 10 g of sodium sulfate. The salts were removed by filtration and the filtrate was distilled in vacuo. Yield: 204 g of α-bromopropionaldehyde dimethylacetal, b.p. 66°–74° C./25 mm Hg.

B—4-Heptynal dimethylacetal

In a 1 l reaction vessel 0.1 g of ferric nitrate was added to 0.75 l of liquid ammonia. 3.5 g (0.5 gramatom) of lithium was then added in small portions in 0.5 hrs and the mixture is stirred until a light grey reaction mixture was obtained. Subsequently, 0.1 g of triphenylmethane was added, the contents of the vessel colouring red. Butyn-1 was introduced until the colour had changed to black (34 g=0.63 mol in all). The vessel contents were stirred during an additional 15 min, liquid ammonia being added if necessary. 0.5 mol of α-bromopropionaldehyde dimethylacetal was then added in 1.5 hrs. Subsequently, the reaction mixture was stirred during 1.5 hrs.

Remark: By refilling a few times, care should be taken that during the reaction vessel will contain a minimum of 0.5 l of liquid ammonia.

The ammonia was then evaporated off and the following was successively added to the residue: 105 g of hexane, 25 g of methanol to destroy the residing lithium rests, 105 ml of water. The mixture was vigorously stirred and then filtered. The hexane layer was separated from the filtrate and the aqueous layer once extracted with 50 g of hexane. The combined hexane solutions were twice washed with water, dried on sodium sulfate and the evaporated in vacuo. The evaporation residue was further distilled in vacuo.

Yield: 70 g (90%) of 4-heptynal dimethylacetal, b.p. 88° C./15 mm Hg.

C—4-Heptynal

A mixture of 200 g of acetone, 51 g (0.33 mol) of 4-heptynal dimethylacetal, 0.2 g of hydroquinone and 9 g of oxalic acid was heated to 50° C. under nitrogen. At this temperature 225 g of water was added in 0.5 hrs and the mixture was stirred for an additional 0.5 hrs. After cooling the acetone was evaporated in vacuo. The remaining mixture was then extracted four times with ether. The ether extracts were washed with a 5% NaHCO$_3$ solution and subsequently with water until neutral. The ether solution was dried on Na$_2$SO$_4$ and evaporated.

Yield: 36 g (99%) of pure 4-heptynal, b.p. 34° C./1 mm Hg.

EXAMPLE II

Preparation of cis-4-heptenal 11 g of 4-heptynal was dissolved in 100 ml of ethanol and after addition of about 100 mg of Lindlar catalyst hydrogenated at room temperature at atmospheric pressure. After absorption of one mol equivalent hydrogen, the hydrogenation velocity visibly decreased. The catalyst was filtered off and the filtrate was evaporated. The residue was distilled in vacuo.

Yield: 10.5 g (94%) of cis-4-heptenal, b.p. 41° C./10 mm Hg.

EXAMPLE III

Preparation of 2,6-nonadiene nitrile

Under reflux 15 g of cis-4-heptenal was added to a solution of 12 g of cyanoacetic acid and a spatula point of β-alanine in 150 ml benzene. With the aid of a Dean-Stark apparatus 2 ml of water was removed. The reaction mixture was then evaporated and the residue was dissolved in 300 ml of pyridine under addition of a spatula point of copper powder. The mixture was refluxed during 1.5 hrs, after which the excess of pyridine was removed by distillation. The residue was distilled in vacuo.

Yield: 7 g (40%) of 2,6-nonadiene nitrile, b.p. 75° C./5 mm Hg. The product was contaminated by a slight, olfactorily non-interfering amount of 3,6-nonadiene nitrile.

EXAMPLE IV

A perfume composition for use in detergents was prepared according to the following recipe:

| | |
|---|---|
| 130 | parts by weight of benzyl salycilate |
| 130 | parts by weight of phenyl ethanol |
| 120 | parts by weight of α-pentyl cinnamic aldehyde |
| 100 | parts by weight of geraniol |
| 80 | parts by weight of benzyl acetate |
| 80 | parts by weight of nonyl acetate |
| 60 | parts by weight of amyl salicylate |
| 60 | parts by weight of linalole |
| 68 | parts by weight of lavandinoline |
| 30 | parts by weight of petit-grain oil |
| 20 | parts by weight of p-t.butyl dihydro cinnamic aldehyde |
| 20 | parts by weight of cinnamic alcohol |
| 25 | parts by weight of musk ketone |
| 15 | parts by weight of musk ambrette |
| 15 | parts by weight of trichloromethyl-phenyl-carbinyl acetate |
| 10 | parts by weight of methyl cinnamate |
| 5 | parts by weight of methyl-β-naphtyl ketone |
| 10 | parts by weight of 4(4-hydroxy-4-methylpentyl)-cyclohexene-3-carbaldehyde |
| 15 | parts by weight of eugenol |
| 3 | parts by weight of methylnonyl-acetaldehyde |
| 3 | parts by weight of undecylene aldehyde |
| 1 | parts by weight of 2,6-nonadiene nitrile (10% solution in diethylphthalate) |
| 1000 | |

EXAMPLE V

A perfume composition of the "Violet-Bouquet" type was prepared according to the following recipe:

| | |
|---|---|
| 250 | parts by weight of bergamot oil (bergaptene-free) |
| 150 | parts by weight of α-isomethylionone |
| 80 | parts by weight of vetiveryl acetate |
| 60 | parts by weight of hydroxycitronellal |
| 50 | parts by weight of Jasmin(1) |
| 30 | parts by weight of musk ambrette |
| 25 | parts by weight of mousse absolute |
| 50 | parts by weight of rose base |
| 30 | parts by weight of East-Indian sandalwood oil |
| 50 | parts by weight of phenyl ethanol |
| 50 | parts by weight of α-pentyl cinnamic aldehyde |
| 25 | parts by weight of heliotropine |
| 50 | parts by weight of bois-de-rose oil |
| 50 | parts by weight of nerolidol |
| 40 | parts by weight of phenylethyl methylethyl carbinol |
| 10 | parts by weight of 2,6-nonadiene nitrile (1% solution in diglycolmonoethylether) |
| 1000 | |

(1) Perfume base of Naarden International N.V.

A.

$$CH_2=CH-CHO + HX + 2ROH \longrightarrow XCH_2CH_2CH(OR)_2$$
$$\phantom{CH_2=CH-CHO + HX + 2ROH \longrightarrow} 2.$$

$$CH_3CH_2C\equiv CH + MeNH_2 \longrightarrow CH_3CH_2C\equiv CMe + NH_3$$
$$\phantom{CH_3CH_2C\equiv CH + MeNH_2 \longrightarrow} 3.$$

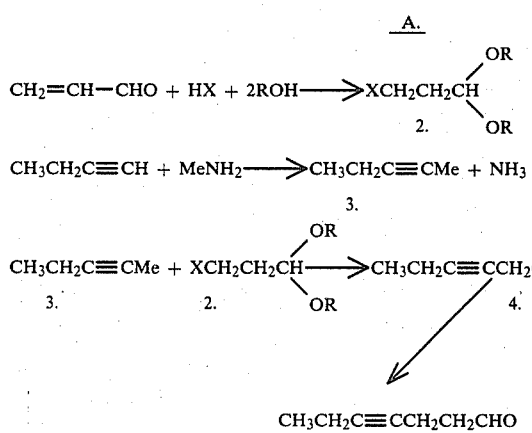

$$CH_3CH_2C\equiv CCH_2CH_2CHO$$
$$1.$$

B.

$$CH_3CH_2C\equiv CCH_2CH_2CHO + NCCH_2COOH \longrightarrow$$
$$1.$$

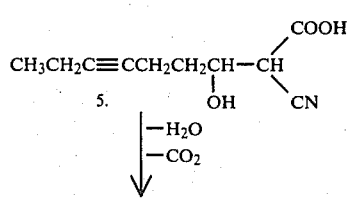

-continued

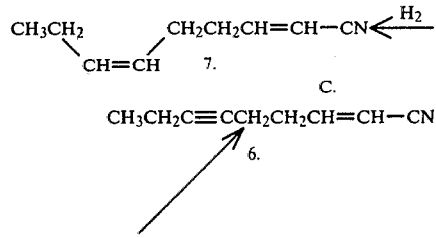

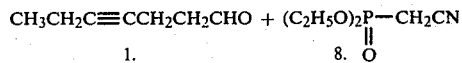

CH₃CH₂C≡CCH₂CH₂CHO + (C₂H₅O)₂P—CH₂CN
1.                          ‖
                         8. O

We claim:
1. A process for the preparation of the compound 4-heptynal-acetal comprising the following steps:
   (a) reacting butyn-1 with an alkalimetal-amide in a polar solvent at a temperature of between about −80° C. and +80° C. to form a solution of alkalimetal butynilide;
   (b) reacting acrolein with a hydrogen halide and a lower aliphatic or araliphatic alcohol having no more than eight (8) carbon atoms, or an aliphatic diol, at a temperature of between about −80° C. and +80° C. to form α-halopropionaldehyde acetal; and
   (c) reacting the α-halopropionaldehyde acetal formed in step (b) with the alkalimetal butynilide formed in step (a) to form the compound 4-heptynal-acetal.

2. A process according to claim 1 wherein the compound 4-heptynal-acetal is subjected to acid hydrolysis to form the compound 4-heptynal.

3. A process according to claim 1 wherein in step (a) the alkalimetal is selected from the group consisting of Na or Li and the polar solvent is ammonia.

4. A process according to claim 1 wherein in step (b) the hydrogen halide is hydrogen bromide, an excess of the alcohol is used to provide a solvent medium and the reaction is carried out at a temperature of between about −20° C. and +30° C.

* * * * *